United States Patent [19]
Eilertsen et al.
[11] Patent Number: 4,519,934
[45] Date of Patent: May 28, 1985

[54] LIQUID ENZYME CONCENTRATES CONTAINING ALPHA-AMYLASE

[75] Inventors: Jens H. Eilertsen, Virum; Arne D. Fog, Ballerup; Keith Gibson, Hvidovre, all of Denmark

[73] Assignee: Novo Industri A/S, Denmark

[21] Appl. No.: 486,306

[22] Filed: Apr. 19, 1983

[51] Int. Cl.[3] .......................... C11D 7/42; C11D 3/386; C11D 7/50; C12N 9/96

[52] U.S. Cl. .................................. 252/174.12; 252/173; 252/DIG. 12; 252/DIG. 14; 435/188; 435/202

[58] Field of Search .................. 252/174.12, DIG. 12, 252/DIG. 14, 173; 435/188, 202

[56] References Cited

U.S. PATENT DOCUMENTS

| | | | |
|---|---|---|---|
| 3,717,350 | 2/1973 | Ziffer | 252/DIG. 12 |
| 3,819,528 | 6/1974 | Berry | 435/188 |
| 4,111,855 | 9/1978 | Barrat et al. | 252/545 |
| 4,142,999 | 3/1979 | Bloching et al. | 252/117 X |
| 4,238,345 | 12/1980 | Guilbert | 252/DIG. 12 X |
| 4,243,543 | 1/1981 | Guilbert et al. | 252/174.12 X |
| 4,318,818 | 3/1982 | Letton et al. | 252/174.12 |

FOREIGN PATENT DOCUMENTS

| | | | |
|---|---|---|---|
| 749329 | 12/1966 | Canada | 435/188 |

OTHER PUBLICATIONS

Research Disclosure, Dec. 1981, No. 212, pp. 451–452, #21241.

Research Disclosure, May 1982, No. 217, p. 170, #21751.

*Primary Examiner*—John E. Kittle
*Assistant Examiner*—Mukund J. Shah
*Attorney, Agent, or Firm*—Fidelman, Wolffe & Waldron

[57] ABSTRACT

A liquid enzyme concentrate containing the alpha-amylase from *Bacillus licheniformis* and optionally a proteinase dissolved in 40–95% by weight propylene glycol 1,2 balance water, at pH 5–9, the enzyme activity being 10–1000 KNU/g of concentrate.

Proteinase may be present in activity of 0.5–6.5 Anson units/g of concentrate. *Subtilisin Carlsberg* is a preferred proteinase, and in such instance, appropriate stabilizers for the proteinase are included in the concentrate.

8 Claims, No Drawings

LIQUID ENZYME CONCENTRATES CONTAINING ALPHA-AMYLASE

The present invention relates to alpha-amylase containing liquid enzyme concentrates adapted for incorporation into liquid detergent formulations.

Incorporation of enzymes, particularly of a proteinase, into liquid detergent formulations has long been an objective of workers in the detergent art. A particular difficulty that faced the art has been the rapid decrease of proteinase enzyme activity which occurred during storage of the liquid detergent product. To a substantial extent, the difficulty has been resolved by the art through inclusion of enzyme stabilizing ingredients such as lower alcohols, calcium ions, and organic acids. (See, for example, the teachings in U.S. Pat. Nos. 4,111,855 and 4,318,818.)

Successful stabilization of enzymatic detergent formulations imposed a requirement upon the producers of the enzyme to supply the enzyme in a form suited to use in the liquid formulations. Desirably, the enzyme supplier should provide a liquid enzyme concentrate adapted to the liquid detergent formulation; indeed, the text of U.S. Pat. No. 4,318,818 appears to indicate that the stabilization system described therein is as applicable to liquid enzyme concentrates as to liquid detergent formulations.

However, the enzyme supplier must be concerned with storage stability of the enzyme concentrate as such, since significant delays can be encountered between preparation of the liquid enzyme concentrate by the enzyme supplier and delivery thereof to the detergent formulator. Both enzyme supplier and detergent formulation would be pleased if the liquid enzyme concentrate exhibited high enough stability to allow also for reasonable delay between delivery of the concentrate and dilution thereof into the detergent formulation without the need for cold storage.

Physical stability, i.e., the stability against phase separation or precipitation, both in regard to the liquid enzyme concentrate and the enzyme containing liquid detergent, is at least as important to all concerned with the detergent as the stability of enzyme activity.

Furthermore, the color and odor of the liquid enzyme concentrate should be such that admixture of the liquid enzyme concentrate into the liquid detergent does not generate any significant change in the color and odor of the liquid detergent.

Although the above discussion to incorporation of enzymes into liquid detergents has been couched in terms generic to all enzymes, the attention of the art was concentrated upon proteinases. Other enzymes, however, are of interest to the detergent art. In particular, alpha-amylase as an enzyme additive to liquid detergent formulations has been of increasing interest in the art in recent years. One commercially available alpha-amylase suitable for additive purposes in liquid detergents is the alpha-amylase of *Bacillus licheniformis*, e.g., Thermamyl®. This alpha-amylase is available as a liquid phase product.

Commercially available liquid *Bacillus licheniformis* alpha-amylase preparations normally have activities between 50 and 150 KNU/g (the KNU alpha-amylase activity unit being defined in AF 9/-GB, obtainable from NOVO INDUSTRI A/S, 2880 Bagsvaerd, Denmark). Such preparations, however, often contain up to 20% w/w of NaCl which component in the enzyme preparation is not desirable in liquid detergents because of the potential for phase separation problems that might result in the liquid detergent from the high salt concentration, and because the chloride ion could corrode metal containers and equipment. In addition, the commercial liquid phase alpha-amylase preparations often are dark in color, have a strong odor and exhibit a tendency to form precipitate on storage. The above described properties impose difficulties on efforts by the liquid detergent producer to formulate a cosmetically acceptable product from the commercially available *Bacillus licheniformis* alpha-amylase liquid preparations and such preparations have not won ready acceptance by the detergent industry.

The object of the invention is to provide a liquid enzyme concentrate containing the alpha-amylase of *Bacillus licheniformis* in higher concentration than has hitherto been available, which concentrate exhibits satisfactory enzymatic and physical stability, does not present any color or odor problems and is non-corrosive.

A further object of this invention is to provide a liquid enzyme concentrate containing both the alpha-amylase of *Bacillus licheniformis* and a proteinase, preferably *Subtilisin Carlsberg.*

The liquid enzyme concentrate of alpha-amylase from *Bacillus licheniformis* according to the invention comprises:

the alpha-amylase from *Bacillus licheniformis* in a concentration corresponding to an activity of between 10 and 1000 KNU/g of concentrate, preferably between 25 and 600 KNU/g of concentrate, more preferably between 250 and 350 KNU/g of concentrate;

propylene glycol 1,2 in an amount of about 40 to about 95% by weight, preferably about 60 to 85% by weight of the concentrate;

water in an amount of about 50% to about 5% by weight, preferably about 30% to about 10% by weight of the concentrate;

the pH of the concentrate is 5–9, preferably 6–7.5.

Thus, surprisingly it has been found that the liquid alpha-amylase concentrate according to the invention exhibits a satisfactory enzymatic and physical stability and does not present color or odor problems. Furthermore, it has been found possible to obtain a liquid enzyme concentrate with far higher alpha-amylase unit activity than is present in the commercially available liquid enzyme concentrates containing the alpha-amylase of *Bacillus licheniformis.* Also, stabilizers of the enzyme in the concentrate, such as those suggested in U.S. Pat. No. 4,318,818 are not needed to maintain satisfactory stability for the alpha-amylase.

The liquid enzyme concentrate according to the invention will contain low levels of inorganic material (ash), 0.5% to 3% w/w. The chloride ion concentration is typically less than 1. Normally, a substantial part of the ash is NaCl and/or $Na_2SO_4$.

As has already been indicated, the enzyme of principal interest of the detergent arts heretofore has been proteinase. Mostly, if not entirely, the alpha-amylase would be present in the final detergent formulation as an additional enzyme activity. The likelihood that the proteinase will degrade all other enzymes, and specifically any alpha-amylase present, must always be considered when a liquid form detergent with multiple enzymes is contemplated. Although a mixed enzyme liquid concentrate of both alpha-amylase and proteinase would be a desirable product, it might be expected that the proteinase would decompose the alpha-amylase therein.

Surprisingly, it has been found that it is possible to provide a mixed proteinase and alpha-amylase concentrate. In particular, a proteinase concentrate prepared as described in patent application, Ser. No. 448,374, filed Dec. 9, 1982 together with a *Bacillus licheniformis* alpha-amylase concentrate prepared as described herein may be combined, so that the resulting liquid concentrate mixture contains therein 0.5 to 6.5 Anson units/g of the total concentrate, preferably 1 to 4 Anson units/g of concentrate and 10 to 400 KNU/g of concentrate, preferably 25 to 200 KNU/g of concentrate without either of the enzyme components therein becoming unstable and without precipitation problems.

The stabilizer ingredients required for best results in the instance of *Subtilisin Carlsberg* as the proteinase do not affect the alpha-amylase detrimentally. Their presence in a mixed enzyme concentrate is a preferred mode of the invention. Reference is made to the aforementioned application, Ser. No. 448,374, for full details of the stabilized *Subtilisin Carlsberg* concentrate. It is noted, however, that not all proteinases suited to detergent usage require presence of the stabilizing ingredients, Savinase® and Esperase® for example. Liquid enzyme concentrates with the alpha-amylase and one of such proteinases would, of course, not require presence of stabilizers.

A preferred embodiment of liquid enzyme concentrate containing an alpha-amylase from *Bacillus licheniformis* according to practice of this invention contains also:

*Subtilisin Carlsberg* in a concentration corresponding to an activity between 0.5 and 6.5 Anson units/g of concentrate, preferably between 1 and 4 Anson units/g of total concentrate;

calcium ion and water soluble carboxylate in concentrations set out by the aforementioned Ser. No. 448,374, with the proviso that the alpha-amylase is present in a concentration corresponding to an activity of between 10 and 400 KNU/g of concentrate, preferably between 25 and 200 KNU/g of concentrate.

The propylene glycol 1,2 content is 60–85% by weight and the pH is 5–8, preferably, pH 6–7.5.

It should be appreciated, however, that not all combinations of alpha-amylase and proteinase activities falling within the above indicated ranges represent commercially useful embodiments of the invention.

Factors extrinsic to practice of this invention, such as storage time and temperatures, the details of customer detergent formulations, even supplier and customer convenience, can dictate preferred enzyme and solvent proportions for the mixed enzyme liquid concentrate modes of this invention. Cut and try testing may be required to establish optimum liquid concentrates. As a practical matter, attempts to employ extremes in all of the above described ranges are to be avoided. Concentrates containing the maximum alpha-amylase activity combined with the maximum proteinase activity may result in a liquid concentrate that relatively soon contains precipitated enzyme. The minimum alpha-amylase activity combined with the minimum proteinase activity may contain too little enzyme to be of practical use in regard to later employment of the liquid enzyme concentrate as an additive to a liquid detergent.

As has been indicated, the liquid enzyme concentrate according to the invention containing the alpha-amylase of *Bacillus licheniformis* is intended for dilution into liquid detergent formulations, typically forming from about 0.1–2% v/v of the final detergent formulation. However, the detergent formulation per se forms no part of this invention. Normally, the enzyme concentrates of this invention will be articles of commerce sold to soapers, who themselves, will incorporate the enzyme concentrate into their own preferred liquid detergent formulations as an enzyme(s) additive therein.

The starting materials for preparing a liquid enzyme concentrate of this invention may be commercially available enzyme solid or liquid enzyme preparations. Liquid alpha-amylase preparations, such as THERMAMYL-120-L for example, can be converted into solid form by salt precipitation and the resulting solid form material employed as described hereinafter. The proteinases widely available commercially in solid form e.g., ALCALASE®, ESPERASE®, may be used, but are not well adapted for practice of this invention. The liquid form proteinases commercially available are better suited to practice of this invention.

Of course, enzyme producers practicing this invention would start preparation of the liquid enzyme concentrate of this invention with some suitable step product less expensive than the standardized in activity enzyme products they market commercially.

To prepare the liquid enzyme concentrate of this invention, the solid form enzyme concentrate, either a solid form concentrated alpha-amylase of *Bacillus licheniformis* alone or a mixture of this alpha-amylase and a solid form concentrated proteinase is extracted with a mixture of propylene glycol 1,2 and water. The extractant may be 100% propylene glycol, if the solid form enzyme concentrate is moist. The resulting slurry is filtered or centrifuged to remove undissolved solids.

The filtrate/supernatant from the slurry may become the finished liquid enzyme concentrate, if such is desired. In the instance when a liquid mixed enzyme concentrate containing both alpha-amylase and *Subtilisin Carlsberg* is being prepared, the propylene glycol-water mixture extractant can be doped appropriately with carboxylate salt and calcium ion beforehand. The proportions of enzyme concentrate to the propylene glycol-water mixture extractant would be selected so the extract filtrate will contain the desired proportions of all ingredients therein.

An alternative method of preparing liquid enzyme concentrates containing both the alpha-amylase and a proteinase is separate preparation of a liquid alpha-amylase concentrate and of a liquid proteinase enzyme concentrate, the latter for example, prepared as is described in Ser. No. 448,374 should *Subtilisin Carlsberg* be the proteinase, followed then by mixing of the two liquid enzyme concentrates in proportions appropriate to the desired final liquid enzyme concentrate product.

The pH of the liquid enzyme concentrates of this invention will ordinarily be in the desired pH 5–8 range, but pH adjustment as necessary, before and/or after inclusion of enzyme(s) into the propylene glycol-water mixture is contemplated. Addition of the $C_1$–$C_3$ carboxylate and of calcium ions to the propylene-glycol water mixture before or after inclusion of the enzymes therein is also contemplated in case a liquid enzyme concentrate containing the alpha-amylase and *Subtilisin Carlsberg* is prepared.

In the following examples describing detailed preferred practice of this invention, one of the features characterizing liquid concentrates which contain only the alpha-amylase enzyme is their relatively low color value. The color value is defined as the optical density at 400 nm of a sample of the liquid enzyme concentrate diluted with water to an enzyme activity of 10 KNU/ml. The color value should be as low as possible. Experience has shown, however, that a color value ≦0.7 is acceptable to manufacturers of liquid detergents. This color value determination is not practical for mixed alpha-amylase/proteinase liquid concentrates because there is an additive color value contribution from both enzymes and a standard activity at which to measure color value has not been defined. In any event, the alpha-amylase liquid enzyme concentrates make a satisfactorily low contribution to the total color value of the mixed enzyme liquid concentrates of this invention.

In the following examples, a solid form alpha-amylase concentrate is used as starting material. Such a solid form alpha-amylase concentrate can be prepared from alpha-amylase solutions varying in activity between 50–150 KNU/g of solution, containing about 18% w/w which is the solid form alpha-amylase concentrate may be dried under vaccuum.

The alpha-amylase employed in the test studies from which the examples are drawn were solutions which otherwise would have been converted into Thermamyl 60-L or 120-L. The solution batches employed in the test studies contained about 100 KNU/g and were converted into solid concentrate as described above.

The proteinase starting material employed to prepare the concentrate of Example 2, was an ALCALASE ® concentrate, produced in accordance with the teachings of Belgium Pat. No. 889,336 which concentrate, however, was not subject to the final drying operation.

For Example 1, tabulated below are the compositions of different liquid enzyme concentrates containing only the alpha-amylase and their properties.

For Example 2, tabulated below are the compositions of different liquid enzyme concentrates containing alpha-amylase and *Subtilisin Carlsberg* and their properties.

| | EXAMPLE 1 | | | | | | |
|---|---|---|---|---|---|---|---|
| Alpha-amylase batch code number | AAH 215 A | AAH 246 A | AAH 246 B | PT 26-1 | PT 24-3 | PT 23-1 | PT 23-4 |
| Alpha-almylase activity in liquid concentrate (KNU/g) | 330 | 138 | 206 | 509 | 257 | 380 | 210 |
| Propylenglycol 1.2 (% w/w) | 77 | 82 | 70 | 54 | 47 | 78 | 78 |
| Water (% w/w) | 18 | 18 | 27 | 38 | 44 | 12 | 17 |
| Chloride (% w/w) | <1 | <1 | 1 | <1 | 1 | <1 | <1 |
| pH | 7.1 | 7.4 | 7.5 | 6.4 | 6.5 | 6.5 | 6.4 |
| Odour | weak | weak | weak | n.a. | n.a. | weak | weak |
| Colour | 0.45 | 0.25 | 0.53 | 0.39 | 0.39 | 0.48 | 0.29 |
| After storage for 4 weeks, 37° C. | | | | | | | |
| alpha-amylase activity (KNU/g) | 328 | 131 | 220 | n.a. | n.a. | 368 | 186 |
| visual appearance | clear, no precipitate | clear, no precipitate | clear, no precipitate | n.a. | n.a. | clear, no precipitate | clear no precipitate |

n.a. = not analyzed

| | EXAMPLE 2 | | | | |
|---|---|---|---|---|---|
| Alpha-amylase batch code number | PT 22-1 | PT 22-2 | PT 33A-1 | PT 33A-2 | PT 33A-4 |
| Alpha-amylase activity in liquid concentrate (KNU/g) | 76 | 58 | 24 | 122 | 256 |
| Proteinase activity in liquid concentrate (AU/g) | 2.1 | 1.6 | 2.6 | 1.9 | 0.9 |
| Propylenglycol 1.2% w/w | 75 | 78 | 75 | 75 | 76 |
| Water % w/w | 20 | 18 | 20 | 20 | 19 |
| Chloride % w/w | <1 | <1 | <1 | <1 | <1 |
| pH | 6.4 | 6.4 | 6.4 | 6.5 | 6.7 |
| Odour | weak | weak | weak | weak | weak |
| After storage for 2 weeks, 37° C. | | | | | |
| Alpha-amylase activity (KNU/g) | 73 | 56 | 24 | 105 | 243 |
| Proteinase activity (AU/g) | 2.1 | 1.6 | 2.6 | 1.9 | 0.9 |
| Visual appearance | clear no, precipitate | clear no precipitate | clear, no precipitate | clear, no precipitate | clear, no precipitate |

n.a. = not analyzed

NaCl, such as Thermamyl 60-L or 120-L in the following manner:

Dilute one part by weight of the alpha-amylase solution with one part by weight of water then heat the mixture to 37° C. Add 0.6 parts by weight of sodium sulphate, stir for 30 minutes then filter. The 37° C. temperature is maintained throughout. The filter cake As may be seen from the data provided in the foregoing Tables of Examples 1 and 2, the liquid enzyme concentrates according to this invention exhibit excellent properties in regard to their physical and enzymatic stability, odor and color.

The procedure described above may be used to prepare concentrates of the alpha-amylase with other proteinases, using for example ESPERASE 8.0 L or SAVINASE 8.0 L as source of the proteinase.

It is claimed:

1. A liquid enzyme concentrate containing alpha-amylase from *Bacillus licheniformis*, which consists essentially of the alpha-amylase from *Bacillus licheniformis* in a concentrate corresponding to an activity of from between 250° and 1000 KNU/g of concentrate;

1,2 propylene glycol in an amount of about 40 to about 95% by weight of the concentrate; and water in an amount of about 50 to about 5% by weight of the concentrate;

whereby the pH of the concentrate is 5–9.

2. The enzyme concentrate of claim 1 wherein pH ranges from 6–7.5.

3. The enzyme concentrate of claim 1 further comprising a propylene glycol 1,2 content in the range of about 60–85% by weight thereof.

4. The enzyme concentrate of claim 1 further comprising presence of the alpha-amylase in an activity range of 250–350 KNU/g of concentrate.

5. The enzyme concentrate of claim 1 further comprising presence of proteinase in an activity range of 1–4 Anson units/g of concentrate.

6. The enzyme concentrate of claim 1 further comprising presence of the alpha-amylase in an activity range of 25–200 KNU/g of concentrate.

7. The enzyme concentrate of claim 6 further comprising presence of *Subtilisin Carlsberg* as the proteinase and stabilizers therefore, in the concentrate.

8. A liquid enzyme concentrate containing alpha-amylase from *Bacillus licheniformis*, which comprises:

the alpha-amylase from *Bacillus licheniformis* in a concentrate corresponding to an activity of from between 10 and 400 KNU/g of concentrate;

a proteinase in a concentration corresponding to an activity of between 0.5 and 6.5 Anson units/g of concentrate;

1,2 propylene glycol in an amount of about 40 to about 95% by weight of the concentrate; and water in an amount of about 50 to about 5% by weight of the concentrate;

the pH of the concentrate being pH 5–9.

* * * * *

UNITED STATES PATENT AND TRADEMARK OFFICE
CERTIFICATE OF CORRECTION

PATENT NO. : 4,519,934
DATED : May 28, 1985
INVENTOR(S) : JENS H. EILERTSEN et al.

It is certified that error appears in the above–identified patent and that said Letters Patent are hereby corrected as shown below:

In Claim 1, line 6:

"250°" should read --250--

In Claims 5 and 6, line 1:

"Claim 1" should read --Claim 8--

Signed and Sealed this

*Fifteenth* Day of *July 1986*

[SEAL]

*Attest:*

DONALD J. QUIGG

*Attesting Officer* *Commissioner of Patents and Trademarks*